(«12) United States Patent
Roth

(10) Patent No.: US 7,495,234 B2
(45) Date of Patent: Feb. 24, 2009

(54) SECURE TAG VALIDATION

(75) Inventor: Joseph D. Roth, Springboro, OH (US)

(73) Assignee: NCR Corporation, Dayton, OH (US)

( * ) Notice: Subject to any disclaimer, the term of this patent is extended or adjusted under 35 U.S.C. 154(b) by 85 days.

(21) Appl. No.: 11/435,929

(22) Filed: May 17, 2006

(65) Prior Publication Data

US 2007/0267581 A1 Nov. 22, 2007

(51) Int. Cl.
*G01N 21/64* (2006.01)

(52) U.S. Cl. .............................. 250/458.1; 250/459.1

(58) Field of Classification Search .............. 250/458.1, 250/459.1
See application file for complete search history.

(56) References Cited

U.S. PATENT DOCUMENTS

| | | | | |
|---|---|---|---|---|
| 4,047,033 | A * | 9/1977 | Malmberg et al. ....... | 250/341.1 |
| 6,297,508 | B1 | 10/2001 | Barmore et al. | |
| 6,510,237 | B1 | 1/2003 | Peltie et al. | |
| 6,678,577 | B1 | 1/2004 | Stylli et al. | |
| 7,057,185 | B2 * | 6/2006 | Curry et al. ............. | 250/459.1 |
| 7,079,230 | B1 | 7/2006 | McInerney et al. | |
| 2004/0031931 | A1 | 2/2004 | Muller et al. | |
| 2005/0178841 | A1 | 8/2005 | Jones et al. | |
| 2006/0086901 | A1 | 4/2006 | Price et al. | |

2007/0145293 A1 6/2007 Roth

FOREIGN PATENT DOCUMENTS

| | | |
|---|---|---|
| EP | 1 158 459 | 11/2001 |
| GB | 2 366 371 A | 3/2002 |
| JP | 49099609 | 9/1974 |
| JP | 49099610 | 9/1974 |
| JP | 01182738 | 7/1989 |
| WO | WO 2007/057641 A1 | 5/2007 |

OTHER PUBLICATIONS

Officer S et al.: "Novel online security system based on rare-earth-doped glass micro beads", Proceedings of the SPIE, SPIE, Bellingham VA US, vol. 5310, No. 1, Jan. 20, 2004, pp. 387-395.

* cited by examiner

*Primary Examiner*—Constantine Hannaher
(74) *Attorney, Agent, or Firm*—Christopher P. Ricci; Charles Q. Maney

(57) ABSTRACT

A device for validating a secure tag comprises: an optical source (such as one or more LEDs); a processor coupled to the optical source for controlling emissions therefrom; and a luminescence detector coupled to the processor. The processor is programmed to control the optical source to create a first and a second pulse sequence having first and second excitation parameters respectfully. The processor is also programmed to control the luminescence detector to measure first and second luminescence in response to the first and second pulse sequences respectively. The processor is programmed to validate the secure tag in the event that the first and second luminescence meet an acceptance criterion. A method of validating a secure tag is also described.

9 Claims, 4 Drawing Sheets

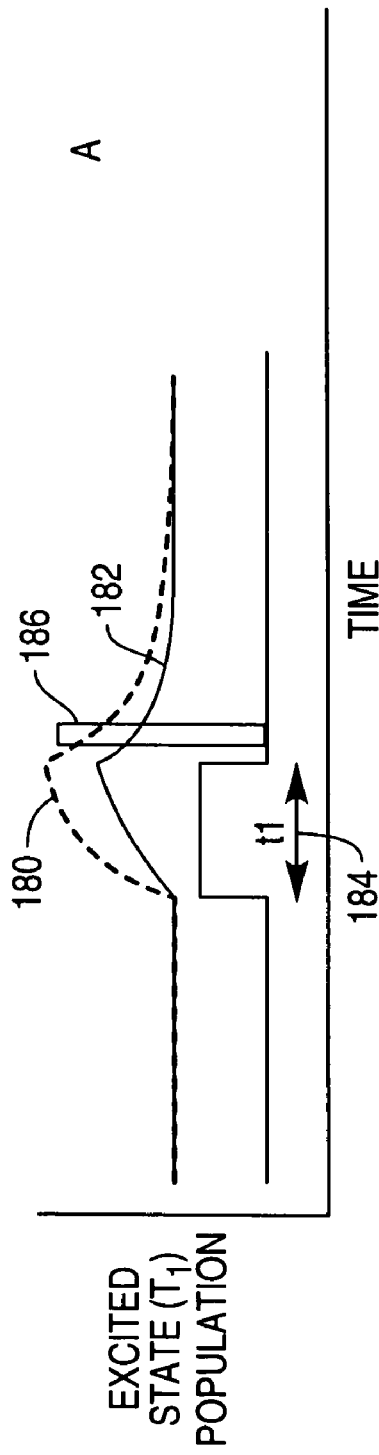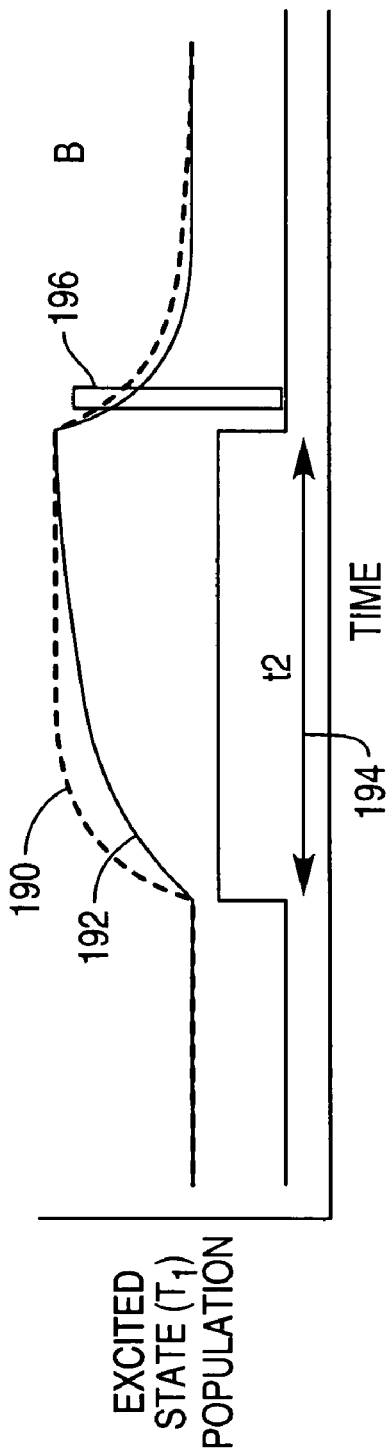

SECURE TAG VALIDATION

The present invention relates to secure tag validation.

BACKGROUND

Secure tags are used for a number of different purposes; a primary purpose being preventing, detecting, and/or deterring counterfeiting of an item to which the secure tag is affixed.

One type of secure tag that has recently been developed includes multiple small particles of a host (such as glass) doped with one or more rare earth ions ("RE ions"). This type of secure tag is described in US patent application number 2004/0262547, entitled "Security Labelling," and US patent application number 2005/0143249, entitled "Security Labels which are Difficult to Counterfeit", both of which are incorporated herein by reference.

These RE particles can be applied to valuable items in different ways. For example, the secure tags can be incorporated in fluids which are applied to valuable items (by printing, spraying, painting, or such like), or incorporated directly into a substrate (paper, metal, rag, plastic, or such like) of the valuable items.

In response to suitable excitation, a secure tag comprising RE particles produces a luminescence spectrum having narrow peaks because of the atomic (rather than molecular) transitions involved. The narrow luminescence peaks result primarily from internal (4f to 4f) transitions of the lanthanide ion. Luminescence is a generic term that relates to a substance emitting optical radiation in response to excitation, and includes photoluminescence.

Photoluminescence is a generic term that includes fluorescence and phosphorescence, which will now be described with reference to FIG. 1, which is a simplified Jablonski energy diagram 10 showing most of the possible transitions in a molecule or atom. In FIG. 1, the wavy lines represent dark transitions (transitions that do not emit or absorb light). The solid lines represent transitions that absorb or emit light.

The molecule or atom starts out in the ground state ($S_0$) 12. When the atom or molecule absorbs light of the appropriate frequency (illustrated by arrows 14 in FIG. 1), electrons in the molecule or atom are promoted to a first singlet excited state ($S_1$) 16 or to a second singlet excited state ($S_2$) 18 (each state having multiple vibrational energy levels). The spin on the promoted electrons are preserved during excitation. The electrons are typically excited to a higher vibrational energy level in the first singlet excited state ($S_1$) 16 before rapidly relaxing (illustrated by arrows 20 in FIG. 1), to the lowest energy level in the first singlet excited state ($S_1$) 16. This event is termed vibrational relaxation or internal conversion and occurs in about a picosecond or less. The excited state may decay directly back to the ground state by way of fluorescence (illustrated by arrows 22), quenching (illustrated by arrow 24), or non-radiative relaxation (illustrated by arrows 26). The excited state may also transfer energy to the triplet excited state ($T_1$) 28, which is referred to as intersystem crossing, as illustrated by wavy line 30. The spin on the electron is flipped as it moves from $S_1$ to $T_1$. From the $T_1$ state the molecule or atom may emit a photon of light (phosphorescence) 32 or lose the energy via non-radiative relaxation 26. During phosphorescence the spin on the electron is again flipped. The transition from $T_1$ to $S_0$ is slow compared to other possible transitions, the timescales are typically between $10^{-3}$ to $10^2$ seconds. Thus, in internal conversion the spin is preserved; whereas in intersystem crossing the spin is flipped.

Secure tags based on RE ions phosphoresce, which allows a delay to be used between excitation and measuring the stimulated phosphorescence. This ensures that any fluorescence from background material (such as a substrate on which the secure tag is located) has decayed prior to the phosphorescence measurements taking place.

To enable quick and accurate validation of a secure tag, a luminescence signature is typically derived from the luminescence measured from that secure tag. This luminescence signature may be based on peak locations, absence of peaks, relative peak intensities, and such like. A luminescence signature is typically derived by converting a large number of data points from a luminescence spectrum into a relatively short code. This short code (the luminescence signature) enables rapid comparison with other, pre-stored luminescence signatures to facilitate validation of the secure tag.

It would be desirable to increase the security of secure tags based on RE particles to make them even more difficult to counterfeit, without making validation of the RE particles slower or more expensive.

SUMMARY

According to a first aspect of the present invention there is provided a secure tag validation method comprising: illuminating the secure tag using a first pulse sequence having first excitation parameters; measuring first luminescence emitted from the secure tag in response to the first pulse sequence; illuminating the secure tag using a second pulse sequence having second excitation parameters; measuring second luminescence emitted from the secure tag in response to the second pulse sequence; validating the secure tag in the event that the first and second luminescence meet an acceptance criterion.

The first excitation parameters may be selected to ensure that an intermediate state is saturated, so that the system is stable and the number of electrons entering the intermediate state is approximately equal to the number of electrons leaving the intermediate state.

The second excitation parameters may be selected to ensure that an intermediate state is not saturated, so that the number of electrons entering the intermediate state exceeds the number of electrons leaving the intermediate state.

The secure tag may include a plurality of rare earth (RE) ions, each RE ion having a different charging time; that is, the time taken to reach saturation for a constant excitation power and frequency.

Where two RE ions are used, one pulse sequence may cause both a first and a second RE ion to saturate; another pulse sequence may cause the first RE ion to saturate, but the second RE ion not to saturate. Where three or more RE ions are used, more permutations are possible.

By virtue of this aspect of the invention, two different excitation pulse sequences can be used to stimulate luminescence from a secure tag. Where multiple different types of RE ions are used in the secure tag, the RE ions will typically have different charging rates. By selecting at least one set of excitation parameters that does not saturate excited triplet states within all of the RE ions, the first luminescence will differ from the second luminescence. This difference can be used to improve security because a counterfeit secure tag is unlikely to replicate this effect.

Those of skill in the art will recognize that to excite a large number of molecules into the $T_1$ state (FIG. 1), a large number of molecules must remain in the $S_1$ state for a substantial period of time. The number of molecules in the $S_1$ excited state is determined by the power and frequency of the illumination. The duration of the pulse determines how much time the molecules have to transition from the $S_1$ state to the $T_1$ state. Because a transition from the $S_1$ state to the $S_0$ state is much more probable than a transition from the $S_1$ state to the $T_1$ state (due to the requirement for the electron spin to flip for the $S_1$ to $T_1$ transition), the $S_1$ state is typically empty within $10^{-9}$ to $10^{-7}$ seconds after the illumination is switched off.

When the illumination is in the form of a relatively short pulse (of constant illumination power and frequency), relatively few molecules enter the $T_1$ state. As the duration of the pulse is increased, the number of molecules entering the $T_1$ state continues to increase. However, at some point the duration of the pulse reaches a certain value (referred to herein as the "saturation time") at which the number of molecules entering the $T_1$ state (through intersystem crossing) equals the number of molecules leaving the $T_1$ state (through phosphorescence and non-radiative relaxation). This state is referred to as saturation. Any increase in the duration of the illumination beyond the saturation time will not increase the amount of phosphorescence after the illumination is turned off. However, if illumination is used that has a pulse duration shorter than the saturation time, then one RE ion may phosphoresce more strongly than another RE ion because of more efficient filling of the $T_1$ state.

The acceptance criterion may be implemented by deriving a first luminescence signature from the measured first luminescence; ascertaining if the derived first luminescence signature matches a first pre-stored luminescence signature; deriving a second luminescence signature from the measured second luminescence; ascertaining if the derived second luminescence signature matches a second pre-stored luminescence signature; and validating the secure tag in the event that the first luminescence signature matches the first pre-stored luminescence signature and the second luminescence signature matches the second pre-stored luminescence signature.

Ascertaining if the derived first luminescence signature matches the first pre-stored luminescence signature may comprise ascertaining whether the derived luminescence signature differs from the first pre-stored luminescence signature by less than a predetermined amount (for example, a five percent difference). In other words, the derived luminescence signature may match the first pre-stored luminescence signature even if there is a relatively small difference between them. Similarly, the second luminescence signature may match the second pre-stored luminescence signature if the difference is less than a predetermined amount.

The first and/or second pulse sequence may be a single pulse, or it may be a series of pulses. Where a series of pulses is used, the repetition rate is the pulse to space ratio for that series.

The excitation parameters may include: excitation frequency, pulse width (that is, the duration of each pulse), pulse power, repetition rate of each pulse (where a pulse sequence comprises a series of pulses), number of pulses in the sequence, and such like.

The step of measuring the first luminescence emitted from the secure tag in response to the first pulse may occur at a time delay ($t_D$) after the illuminating step has ceased; that is, without any illumination present (no pulse sequence). Alternatively, the step of measuring the first luminescence emitted from the secure tag in response to the first pulse occurs simultaneously with the illuminating step.

Preferably, the time delay ($t_D$) is selected to ensure that background fluorescence has decayed to noise levels prior to the measuring steps taking place. The time delay ($t_D$) may be between 5 and 2500 microseconds.

To achieve a stronger signal, the method may involve taking multiple measurements at the same delay time before a secure tag is validated. For example, a secure tag may be excited, the time delay ($t_D$) elapses, the luminescence is measured, the secure tag is then immediately excited again, the same time delay ($t_D$) elapses, the luminescence is measured again, and so on. The multiple measurements (all at the same delay time) are then combined. Although this increases the length of time required to validate a secure tag, it ensures that a short integration time can be used for each measurement.

By changing the parameters of the excitation pulse sequences, the resulting phosphorescent spectrum can be altered. The time scale selected for the pulse width parameter can range from nanoseconds to milliseconds. A similar effect can be achieved by changing the power of the excitation pulse, and (where a series of pulses is used) by changing the repetition rate.

This aspect of the invention has the advantage of added flexibility and security to the tag validation process, without adding much complexity.

According to a second aspect of the invention there is provided a device for validating a secure tag, the device comprising: an optical source; a processor coupled to the optical source; and a luminescence detector coupled to the processor; the processor being operable (i) to control the optical source to create a first and a second pulse sequence having first and second excitation parameters respectfully, (ii) to control the luminescence detector to measure first and second luminescence in response to the first and second pulse sequences respectively, and (iii) to validate the secure tag in the event that the first and second luminescence meet an acceptance criterion.

The device may include a network connection to upload or download data.

These and other aspects of the present invention will be apparent from the following specific description, given by way of example, with reference to the accompanying drawings.

BRIEF DESCRIPTION OF THE DRAWINGS

In the accompanying drawings:

FIGS. 3A and 3B are two graphs illustrating differential rates of saturation from an excited state (the $S_1$ excited state) to an intermediate state (the $T_1$ state) for two different lanthanide ions;

DETAILED DESCRIPTION

Figure 2:
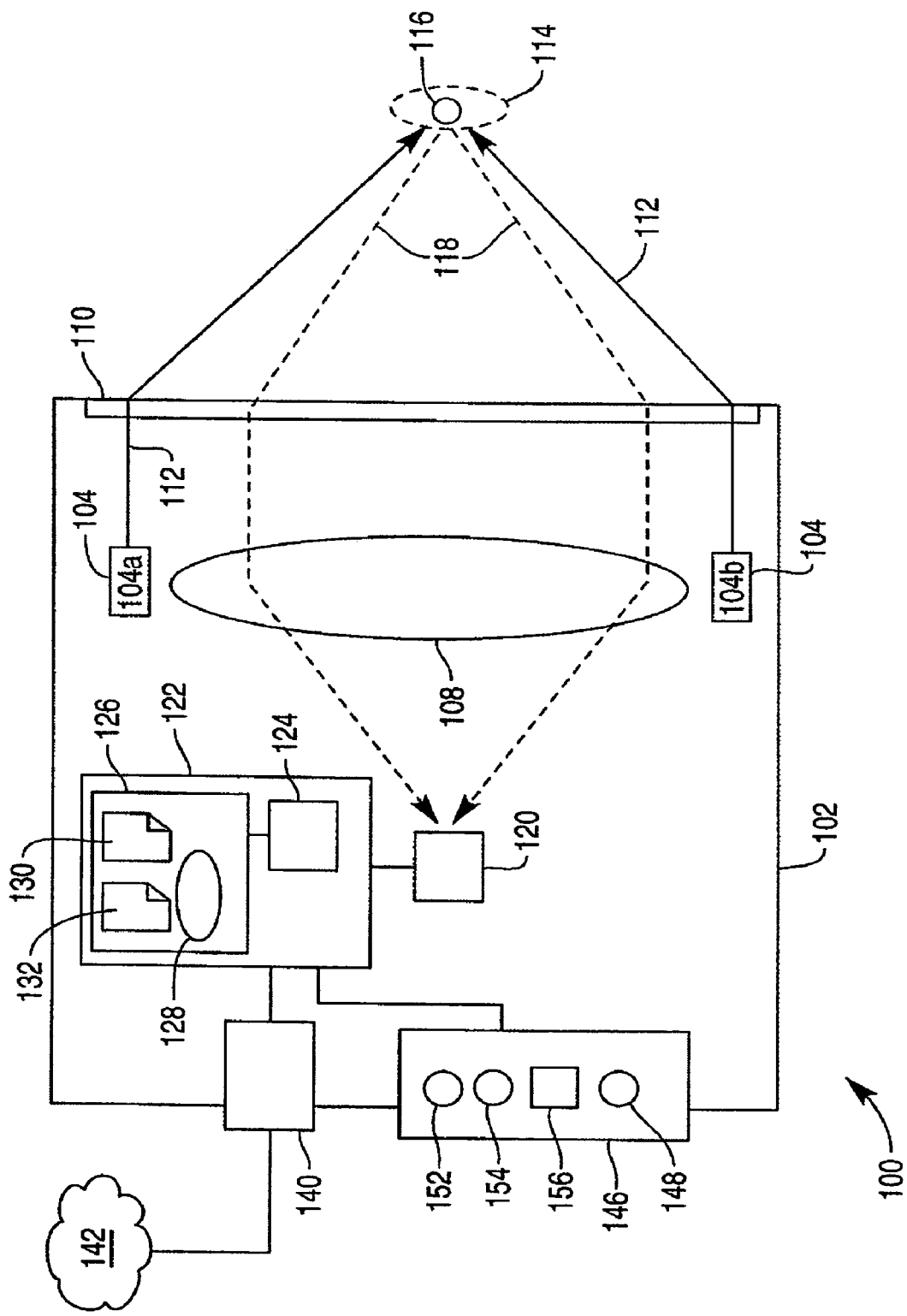
FIG. 2 is a schematic diagram of a secure tag reader according to one embodiment of the present invention.

Reference is first made to FIG. 2, which is a schematic diagram of a secure tag reader 100 according to one embodiment of the present invention.

The reader 100 is a fixed position unit and comprises a housing 102 in which an optical excitation source 104 is mounted. The optical excitation source 104 is in the form of a pair of LEDs 104a, 104b circumferentially spaced around a collecting lens 108, diametrically opposite each other. The LEDs 104a, 104b emit at approximately 395 nm, which is visible to the human eye and corresponds to the deep blue region of the electromagnetic spectrum, and have a power of approximately 8 mW.

A Fresnel lens 110 is mounted at a window in the housing 102 to focus radiation (illustrated by arrows 112) from the excitation source 104 onto a focus spot (illustrated by broken line 114) at which a group of secure tags 116 will be located.

Luminescence emitted from the secure tags 116 (illustrated by broken arrows 118) is directed by the Fresnel lens 110 onto the collecting lens 108, which in turn focuses the luminescence onto a luminescence detector 120, which is an imaging sensor in the form of a CCD sensor.

The CCD sensor 120 is coupled to a controller 122, comprising a processor 124 and non-volatile memory (NVRAM) 126.

The processor 124 receives intensity data from the CCD sensor 120 and processes this data to validate the secure tags 116, as will be described in more detail below.

The NVRAM 126 stores: a processing algorithm 128, a parameter information file 130, and pre-stored luminescence signatures 132.

The processing algorithm 128 is used by the processor 124 to derive luminescence signatures from measured luminescence, and to compare the derived luminescence signatures with the pre-stored luminescence signatures 132.

The parameter information file 130 stores (i) excitation parameters used by the processor 124 to control activation and de-activation of the LEDs 104a, 104b, and (ii) detection parameters used by the processor 124 to control activation of the CCD sensor 120.

There are a plurality of sets of excitation parameters (in this embodiment there are three sets of excitation parameters), where each set of excitation parameters is used to create a pulse sequence. There are also a plurality of pre-stored luminescence signatures 132, with one luminescence signature corresponding to each set of excitation parameters. In this embodiment there are three pre-stored luminescence signatures.

The detection parameters indicate when the CCD sensor 120 is to be activated, and how long an integration time is to be used to measure luminescence, so that the sensor 120 detects (or at least transmits to the processor 124) luminescence when activated by the controller 122. The sensor 120 may actually detect luminescence continually so the processor 124 may only receive (or only store) the detected luminescence when the CCD sensor 120 is "activated". In this embodiment, the detection parameters are the same for each set of excitation parameters.

The controller 122 is coupled to a USB port 140 for outputting data, or the results of analysis on the data, and (in some embodiments) for receiving updated parameter information from a remote source via a network 142.

The reader 100 also includes a simple user interface 146 coupled to the controller 122. The user interface 146 comprises: a trigger 148, which allows a user to activate the reader 100; a red LED 152, which indicates a failure to validate a secure tag; a green LED 154, which indicates a successfully validated secure tag; and a loudspeaker 156, which emits a short beep when a secure tag is successfully validated, and a long beep when a secure tag is not successfully validated.

In this embodiment, the reader 100 is intended to read secure tags 116 comprising microbeads of borosilicate glass doped with 3 mol % of Europium and 3 mol % of Dysprosium. The principles of manufacturing borosilicate glass doped with Europium and Dysprosium are described in US patent application publication number 2005/0143249, entitled "Security Labels which are Difficult to Counterfeit".

Reference is now also made to FIGS. 3A and 3B, which are two graphs illustrating the differential rates of saturation from the $S_1$ excited state to the $T_1$ state for Eu and Dy. In each of these Figs., a single pulse of optical excitation is used; however, the pulse width in FIG. 3A is shorter than that used in FIG. 3B. Population of the triplet state in the Eu ion occurs more quickly than for the Dy ion, so the charging curve 180 of the Eu ion in FIG. 3A is steeper than the curve 182 of the Dy ion. Since the pulse width 184 in FIG. 3A is relatively short, neither the Eu ion nor the Dy ion reaches saturation. A detection window 186 is shown in FIG. 3A, at which the luminescence intensity from the Eu ion is disproportionately greater than the luminescence intensity from the Dy ion, because the Eu ion is nearer saturation (and therefore has a higher triplet state population).

In FIG. 3B, although the charging curve 190 of the Eu ion is steeper than the curve 192 of the Dy ion, both curves reach saturation because the pulse width 194 is relatively long. A detection window 196 is shown in FIG. 3B, at which the luminescence intensity from the Eu ion is only slightly greater than the luminescence intensity from the Dy ion, reflecting the steady state condition of saturation.

To program the secure tag reader 100 to read secure tags comprising Eu and Dy RE ions, excitation parameters are derived. The excitation frequency is 395 nm and the power is 8 mW, which are the characteristics of the LEDs 104a, 104b mounted in the reader 100. The number of pulses, pulse width, and repetition rate can be selected from a number of different variables.

First excitation parameters comprise the pulse width, repetition rate, and number of pulses. The first excitation parameters are selected through trial and error to ensure that both the Eu and Dy ions are saturated as a result of a first pulse sequence based on the first excitation parameters.

Second excitation parameters comprise a shorter pulse width than for the first excitation parameters, but the same repetition rate, and the same number of pulses. The second excitation parameters are selected through trial and error to ensure that the Eu ion is saturated but the Dy ion is not saturated as a result of a second pulse sequence based on the second excitation parameters.

Third excitation parameters comprise a shorter pulse width than for the first or second excitation parameters, but the same repetition rate, and the same number of pulses. The third excitation parameters are selected through trial and error to ensure that neither the Eu ions nor the Dy ions are saturated as a result of a third pulse sequence based on the third excitation parameters.

The first, second, and third excitation parameters are loaded into the parameter information file 130 in reader 100. Detection parameters are also loaded into the parameter information file 130. In this embodiment, the detection parameters, which are used by the processor 124 to control activation of the CCD sensor 120, are set to ten microseconds (10 μs) after a pulse sequence has ceased. In this embodiment, the same detection parameter is used for each pulse sequence.

Figure 1:
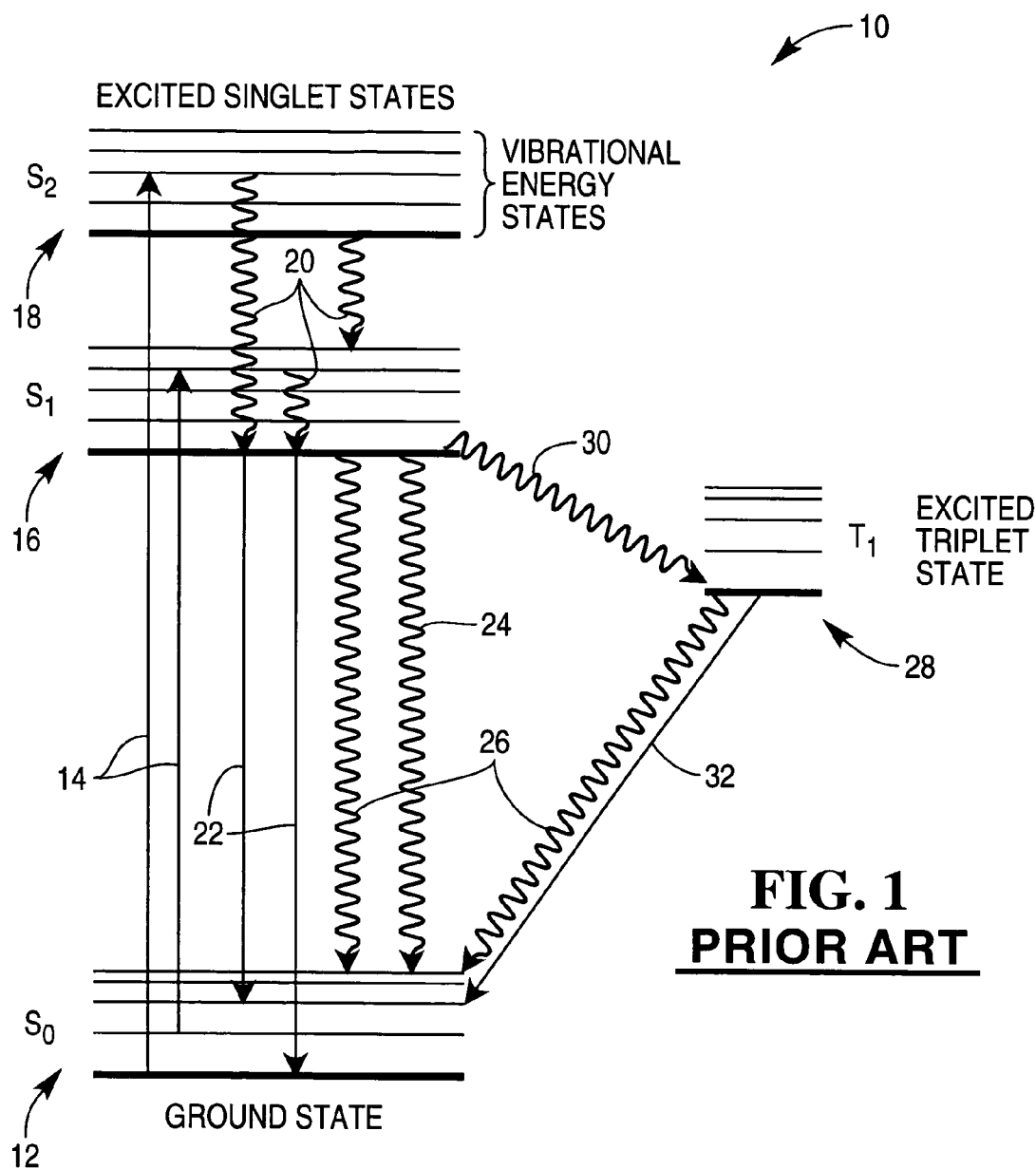
FIG. 1 is a prior art Jablonski energy diagram provided as background information.
Figure 4:
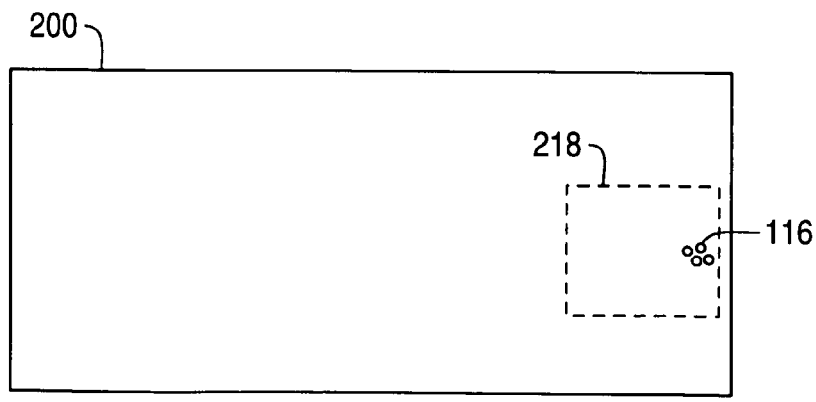
FIG. 4 is a schematic diagram of a banknote incorporating a secure tag for validation by the reader of FIG. 1.
Figure 5:
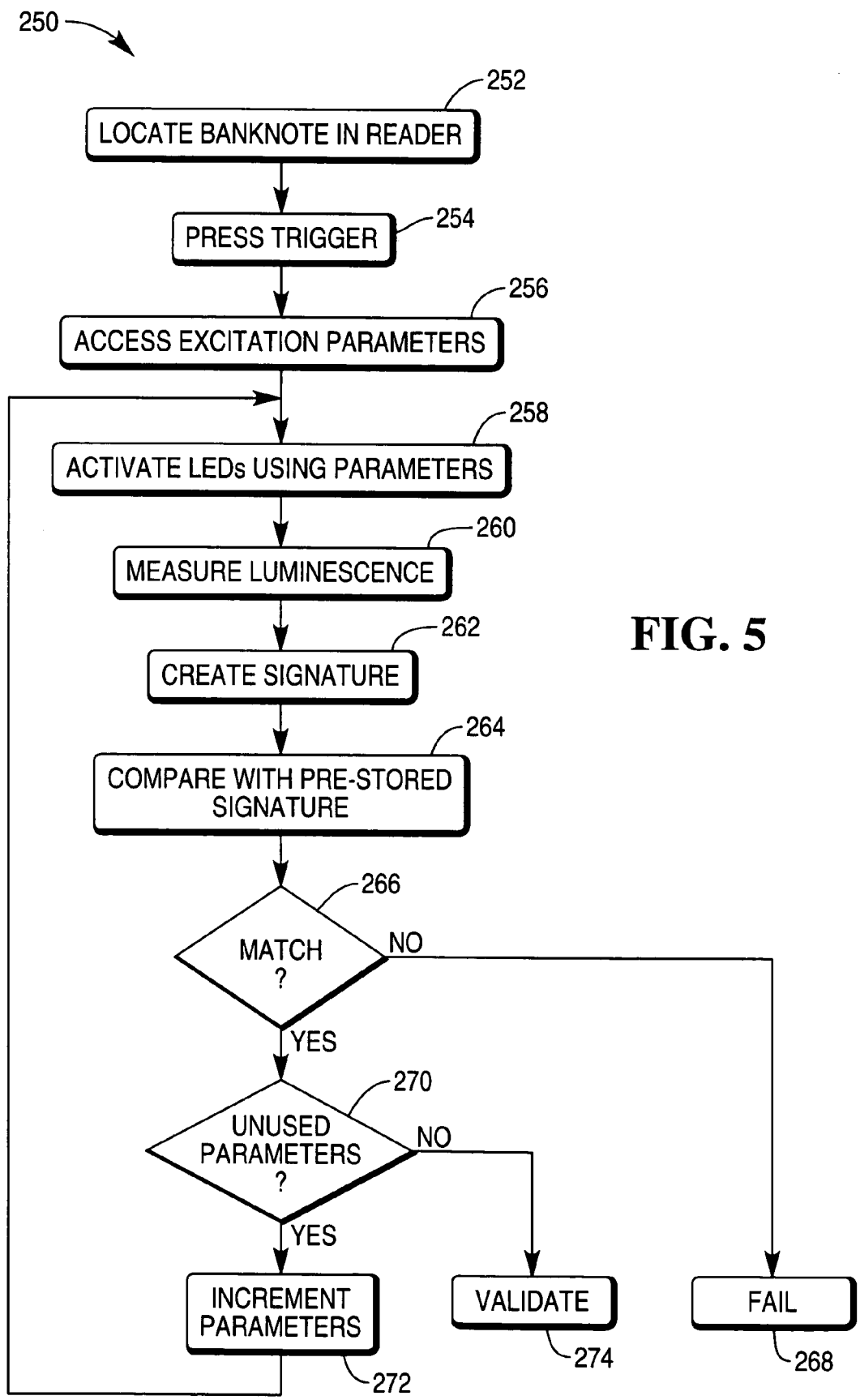
FIG. 5 is a flowchart illustrating steps involved in validating the banknote of FIG. 4 using the reader of FIG. 1.

Once the parameter information file 130 has been loaded, the reader 100 is ready to validate secure tags, as will now be described with reference to FIG. 4 and FIG. 5. FIG. 4 is a schematic diagram of a valuable media item 200, in the form of a banknote, which is printed with ink incorporating secure tags 116 at a tag area 218 on the banknote 200. The tags 116 comprise small beads (typically having an average diameter of five microns or less) of borosilicate glass doped with 3 mol % of Dysprosium and 3 mol % of Europium. For clarity, in FIG. 4 the tags 116 are greatly enlarged with respect to the banknote 200, and only a few tags 116 are shown is a flowchart 250 illustrating steps involved in validating a secure tag. FIG. 5 is a flowchart illustrating steps involved in validating the banknote of FIG. 4 using the reader 100.

The first step (step 252) is for the user to locate the banknote 200 in the reader 100. Once the banknote 200 is correctly aligned, the user presses the trigger 148 (step 254). The banknote 200 and reader 100 are aligned when the reader's focus spot 114 is in registration with the tag area 218. This may be achieved either by moving the banknote 200 or by moving the reader 100, or both.

On receipt of a trigger press, the processor 124 accesses the parameter information file 130 to retrieve the first excitation parameters and detection parameters (step 256). Using the retrieved excitation parameters, the processor 124 creates a first pulse sequence, and applies this first pulse sequence to the LEDs 104a, 104b (step 258). The LEDs 104a, 104b illuminate the secure tags 116 using this first pulse sequence.

Once the first pulse sequence has ended, the processor 124 then applies the retrieved detection parameters to activate the CCD sensor 120 and measure luminescence from the secure tags 116 (step 260). In this embodiment, the detection parameters define a time delay of a hundred microseconds (100 μs), and an integration time (the length of time over which a measurement is recorded) of five hundred microseconds (500 μs).

The processor 124 then derives a luminescence signature from the measured luminescence spectrum of the secure tags 116 using the algorithm 128 (step 262). In this embodiment, the algorithm 128 identifies the peaks in the measured luminescence, normalizes the intensities of the identified peaks, compares the ratios of all of the peaks, and creates a unique code based on the peak ratios. This unique code is the luminescence signature for the secure tags 116 in response to the first pulse sequence.

The processor 124 then compares the derived luminescence signature with the corresponding luminescence signature 132 pre-stored in the NVRAM 126 (step 264) to ascertain if there is a match (step 266). If the two signatures do not meet an acceptance criterion, for example, if the two signatures do not match (within a predetermined tolerance) then the secure tag 116 is not validated (step 268), and the processor 124 activates the red LED 152 and causes the loudspeaker 156 to emit a long beep.

If the two signatures do meet an acceptance criterion, for example, if the two signatures match (within a predetermined tolerance) then the processor 124 ascertains if there are any unused sets of excitation parameters (step 270).

If there are more unused sets of excitation parameters then the processor 124 increments to the next set of excitation parameters and loops back to step 258 (step 272). The processor 124 then uses this next set of excitation parameters to generate a another pulse sequence. This continues until there are no more sets of excitation parameters.

If there are no more unused sets of excitation parameters then the secure tags 116 are validated (step 274) and the processor 124 activates the green LED 154 and causes the loudspeaker 156 to emit a short beep.

This embodiment provides increased security because different pulse sequences are used, each corresponding to a different charge state, so each stimulates a different luminescence signature. It would be extremely difficult to replicate these luminescence signatures using a different substance than the RE ions being used.

Various modifications may be made to the above described embodiment within the scope of the present invention, for example, in other embodiments a secure tag based on luminescent particles other than rare earth doped hosts may be used. Where rare earth doped hosts are used, more or fewer than two rare earth ions may be included in each secure tag. The rare earth ion or ions used may be different to Europium and Dysprosium. The rare earth ions may comprise lanthanide ions. In other embodiments, rare earth ions may be incorporated in hosts other than glass.

In the above embodiment, the same detection parameters are used for each pulse sequence; in other embodiments, each pulse sequence may have different detection parameters.

In the above embodiment, luminescence was measured after excitation ceased; however, in other embodiments, luminescence measurements may be recorded while the secure tag is being excited.

The detection parameters may be different to those described above.

In the above embodiment, the luminescence signatures were derived from the peaks in the wavelength range; in other embodiments, different parts of a luminescence spectrum may be used, for example, fewer than all of the peaks, areas of the wavelength range that are not peaks, for example, areas of background noise, or areas part-way between a peak and background noise.

What is claimed is:

1. A secure tag validation method comprising:
    illuminating the secure tag using a first pulse sequence having first excitation parameters;
    after a first time-delay following cessation of the first pulse sequence, measuring first luminescence emitted from the secure tag in response to the first pulse sequence;
    illuminating the secure tag using a second pulse sequence having second excitation parameters;
    after a second time-delay following cessation of the second pulse sequence, measuring second luminescence emitted from the secure tag in response to the second pulse sequence; and
    validating the secure tag in the event that the first and second luminescence meet an acceptance criterion.

2. The method of claim 1, wherein the first excitation parameters are selected to ensure that an intermediate state is saturated.

3. The method of claim 1, wherein the second excitation parameters are selected to ensure that an intermediate state is not saturated.

4. The method of claim 1, wherein the secure tag includes a plurality of rare earth ions, each rare earth ion having a different charging time.

5. The method of claim 1, wherein the acceptance criterion is implemented by:
    deriving a first luminescence signature from the measured first luminescence;
    ascertaining if the derived first luminescence signature matches a first pre-stored luminescence signature;
    deriving a second luminescence signature from the measured second luminescence;
    ascertaining if the derived second luminescence signature matches a second pre-stored luminescence signature; and
    validating the secure tag in the event that the first luminescence signature matches the first pre-stored luminescence signature and the second luminescence signature matches the second pre-stored luminescence signature.

6. The method of claim 5, wherein ascertaining if the derived first luminescence signature matches the first pre-stored luminescence signature comprises ascertaining whether the derived luminescence signature differs from the first pre-stored luminescence signature by less than a predetermined amount.

7. The method of claim 1, wherein the excitation parameters include:
excitation frequency, pulse width, repetition rate of each pulse, and the number of pulses in the sequence.

8. A device for validating a secure tag, the device comprising:
an optical source;
a processor coupled to the optical source; and
a luminescence detector coupled to the processor;
the processor being operable to (i) control the optical source to create a first and a second pulse sequence having first and second excitation parameters respectively, (ii) control the luminescence detector to, after a time-delay following cessation of each of the first and the second pulse sequences, measure first and second luminescence in response to the first and second pulse sequences respectively, and (iii) validate the secure tag in the event that the first and second luminescence meet an acceptance criterion.

9. The device of claim 8 further comprising a memory coupled to the processor, where the memory holds a plurality of pre-stored luminescence signatures.

* * * * *